(12) United States Patent
Descamps et al.

(10) Patent No.: US 6,984,630 B1
(45) Date of Patent: Jan. 10, 2006

(54) ENDOFUCANASES AND METHOD USING SAME FOR PREPARING FUCO-OLIGOSACCHARIDES FROM FUCANES, BACTERIUM PRODUCING ENDOFUCANASES AND USES OF FUCO-OLIGOSACCHARIDES FOR PLANT PROTECTION

(75) Inventors: Valérie Descamps, Roscoff (FR); Olivier Klarszinsky, Fessenheim (FR); Tristan Barbeyron, Cleder (FR); Bernard Cloarec, Plouenan (FR); Bernard Fritig, Soufelweyersheim (FR); Jean-Marie Joubert, Saint-Malo (FR); Bertrand Plesse, Strasbourg (FR); Jean-Claude Yvin, Saint-Malo (FR)

(73) Assignee: Laboratoires GOEMAR S.A., Saint-Malo Cedex (FR)

( * ) Notice: Subject to any disclaimer, the term of this patent is extended or adjusted under 35 U.S.C. 154(b) by 0 days.

(21) Appl. No.: 09/787,714

(22) PCT Filed: Sep. 21, 1999

(86) PCT No.: PCT/FR99/02243

§ 371 (c)(1),
(2), (4) Date: Mar. 21, 2001

(87) PCT Pub. No.: WO00/17215

PCT Pub. Date: Mar. 30, 2000

(30) Foreign Application Priority Data

Sep. 21, 1998 (FR) .................................. 98 11756

(51) Int. Cl.
*A01N 43/04* (2006.01)
*A61K 31/70* (2006.01)
*A61K 31/715* (2006.01)

(52) U.S. Cl. ............................ 514/54; 514/23; 514/25; 514/61; 514/62

(58) Field of Classification Search ............... 536/55.1, 536/1.11, 17.2, 4.1; 504/100; 514/54, 23, 514/25, 53, 61, 62
See application file for complete search history.

(56) References Cited

U.S. PATENT DOCUMENTS 5,438,124 A * 8/1995 Matta et al.
5,588,254 A * 12/1996 Adachi et al.
6,033,658 A * 3/2000 Ishibashi .................... 424/93.1

OTHER PUBLICATIONS

Patent Abstracts of Japan vol. 95, No. 6, Jul. 31, 1995 & JP 07 059563 A (Tousa Kogaku Kenkyusho), Mar. 7, 1995 *abstract* & Chemical Abstract, vol. 122, No. 21, May 22, 1995 Columbus, Ohio, US ; abstract No. 259851, *abstract*.
Patent Abstracts of Japan vol. 95, No. 11, Dec. 26, 1995 & JP 07 215990 A (Tousa Kogaku Kenkyusho), Aug. 15, 1995 *abstract* & Database WPI Week 9541 Derwent Publications Ltd., London, GB; AN 317479.

* cited by examiner

*Primary Examiner*—James O. Wilson
*Assistant Examiner*—Traviss C. McIntosh III
(74) *Attorney, Agent, or Firm*—McDonnell Boehnen Hulbert & Berghoff LLP (57) ABSTRACT

The invention concerns endofucanases suitable for preparing fuco-oligosaccharides by enzymatic hydrolysis of fucanes. It also concerns a bacterium producing endofucanases and the preparation of said enzyme from the bacterium. It further concerns endofucanase genes and it finally concerns the use said fuco-oligosaccharides for plant protection.

6 Claims, 2 Drawing Sheets

SEQUENCE LISTING

```
<160> NUMBER OF SEQ ID NOS: 6

<210> SEQ ID NO 1
<211> LENGTH: 1474
<212> TYPE: DNA
<213> ORGANISM: Unknown
<220> FEATURE:
<223> OTHER INFORMATION: Gram-negative rod bacterium
<221> NAME/KEY: misc_feature
<222> LOCATION: (12)..(12)
<223> OTHER INFORMATION: "n" = a or g or c or t/u, unknown or other
<221> NAME/KEY: misc_feature
<222> LOCATION: (1124)..(1124)
<223> OTHER INFORMATION: "n" = a or g or c or t/u, unknown or other

<400> SEQUENCE: 1
agagtttgat cntggctcag gatgaacgct agcggcaggc ctaacacatg caagtcgagg      60
ggtagagaga gcttgctttt cttgagaccg gcgcacgggt gcgtaacgcg tatacaatct    120
```

-continued

```
gcctcttact gcgggatagc ccagagaaat ttggattaat atcgcatagc ataacgaccc      180
cgcatgggat gttattaaag gttacggtaa gagatgagta tgcgttctat tagctagatg      240
gagtggtaac ggcacaccat ggcaacgata gatagggggcc ctgagagggg gatcccccac     300
actggtactg agacacggac cagactccta cgggaggcag cagtgaggaa tattggacaa      360
tggaggcaac tctgatccag ccatgccgcg tgcaggaaga cggccctatg ggttgtaaac      420
tgcttttata cgggaagaaa caccgctacg tgtagccttt gacggtaccg taagaataag      480
gatcggctaa ctccgtgcca gcagccgcgg taatacggag gatccaagcg ttatccggaa      540
tcattgggtt taaagggtcc gtagtggatg attaagtcag aggtgaaatc ctgccgctca      600
acggtagaat tgcctttgat actggttatc ttgaatcaat gtgaagtggt tagaatatgt      660
agtgtagcgg tgaaatgcat agatattaca tagaatacca attgcgaagg cagatcacta      720
acattgtatt gacactgatg gacgaaagcg tggggagcga acaggattag ataccctggt      780
agtccacgcc gtaaacgatg gatactagct gttcggattt atctgagtgg ctaagcgaaa      840
gtgataagta tcccacctgg ggagtacgtt cgcaagaatg aaactcaaag gaattgacgg      900
gggcccgcac aagcggtgga gcatgtggtt taattcgatg atacgcgagg aaccttacca      960
gggcttaaat gtagattgca ttaggtggag acacttattt cttcggacca tctacaaggt     1020
gctgcatggt tgtcgtcagc tcgtgccgtg aggtgtcagg ttaagtccta taacgagcgc     1080 aaccccccgtt gttagttgcc agcgagtcat gtcgggaact ctancaagac tgccagtgca     1140
aactgtgagg aaggtgggga tgacgtcaaa tcatcacggc ccttacgtcc tgggctacac     1200
acgtgctaca atggtaggga cagagagcag ccactgggcg accaggagcg aatctataaa     1260
ccctatcaca gttcggatcg gagtctgcaa ctcgactccg tgaagctgga atcgctagta     1320
atcgcatatc agccatgatg cggtgaatac gttcccgggc cttgtacaca ccgcccgtca     1380
agccatggaa gctgggagtg cctgaagtcc gtcaccgcaa ggagcggcct agggtaaaat     1440
cggtaactag ggctaagtcg taacaaggtg tccg                                 1474
```

```
<210> SEQ ID NO 2
<211> LENGTH: 15
<212> TYPE: PRT
<213> ORGANISM: Unknown
<220> FEATURE:
<223> OTHER INFORMATION: Gram-negative rod bacterium

<400> SEQUENCE: 2

Gln Thr Ala Asn Thr Thr Tyr Gly Ile Asn Thr Val Ala Ser Met
1               5                   10                  15

<210> SEQ ID NO 3
<211> LENGTH: 18
<212> TYPE: PRT
<213> ORGANISM: Unknown
<220> FEATURE:
<223> OTHER INFORMATION: Gram-negative rod bacterium
```

-continued

<400> SEQUENCE: 3

```
Thr Ser Gly Pro Asp Trp Leu Thr Ile Gln Gln Thr Asp Ala Asn Ser
1               5                   10                  15

Gly Lys
```

<210> SEQ ID NO 4
<211> LENGTH: 17
<212> TYPE: PRT
<213> ORGANISM: Unknown
<220> FEATURE:
<223> OTHER INFORMATION: Gram-negative rod bacterium

<400> SEQUENCE: 4

```
Ile Thr Val Asp His Val Ala Gly Phe Thr Asn Leu Trp Asn Gly Ala
1               5                   10                  15

Pro
```

<210> SEQ ID NO 5
<211> LENGTH: 203
<212> TYPE: DNA
<213> ORGANISM: Unknown
<220> FEATURE:
<223> OTHER INFORMATION: Gram-negative rod bacterium

<400> SEQUENCE: 5

```
attacggttg atcatgttgc aggttttact aatttgggta atggagcacc tgtttggtct      60
tcacctatac ttaatcttac cgatggaaaa ggatcattcg cctataatta tactttgcaa     120
ttaggaaccg attattatga ttttgaaggt gatgcactta ctattactaa aacatcagga     180
cctgattggc tcaccattca aca                                             203
```

<210> SEQ ID NO 6
<211> LENGTH: 67
<212> TYPE: PRT
<213> ORGANISM: Unknown
<220> FEATURE:
<223> OTHER INFORMATION: Gram-negative rod bacterium

<400> SEQUENCE: 6

```
Ile Thr Val Asp His Val Ala Gly Phe Thr Asn Leu Gly Asn Gly Ala
1               5                   10                  15

Pro Val Trp Ser Ser Pro Ile Leu Asn Leu Thr Asp Gly Lys Gly Ser
            20                  25                  30

Phe Ala Tyr Asn Tyr Thr Leu Gln Leu Gly Thr Asp Tyr Tyr Asp Phe
        35                  40                  45

Glu Gly Asp Ala Leu Thr Ile Thr Lys Thr Ser Gly Pro Asp Trp Leu
    50                  55                  60

Thr Ile Gln
65
```

ENDOFUCANASES AND METHOD USING SAME FOR PREPARING FUCO-OLIGOSACCHARIDES FROM FUCANES, BACTERIUM PRODUCING ENDOFUCANASES AND USES OF FUCO-OLIGOSACCHARIDES FOR PLANT PROTECTION

The invention relates to endofucanases suitable for the preparation of fuco-oligosaccharides by enzymatic hydrolysis of fucanes.

It also relates to a bacterium producing endofucanases and to the preparation of the said enzyme starting from the bacterium.

It furthermore relates to genes of endofucanases.

It finally relates to the use of the said fuco-oligosaccharides for the protection of plants.

Fucanes are polysaccharides based on α-L-fucose.

It is possible to extract fucanes from the wall of brown algae.

This is also possible to extract them from echinoderms.

Oligosaccharidic fractions have already been prepared by acid or radical hydrolyses starting from fucanes.

Various biological activities have been studied as well in respect with fucanes as with certain fractions of lower molecular weight.

The invention relates to particular fuco-oligosaccharides, to an enzyme for their preparation and to their uses in the field of plant protection.

Figure 1:
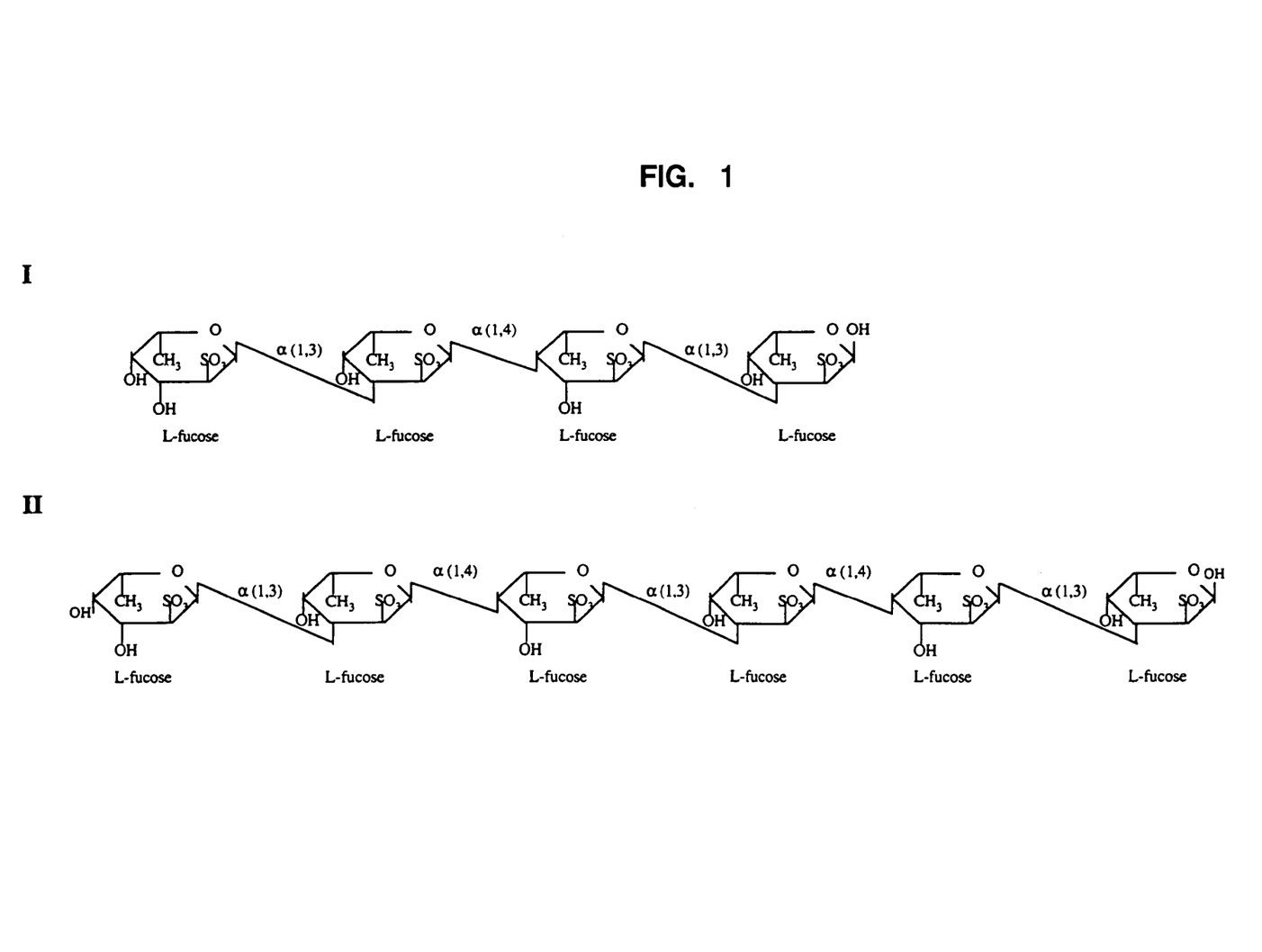

The fuco-oligosaccharides in question are sulphated and have a polymerisation degree from 4 to 100, preferably from 4 to 20 α-L fucose units; two of these fuco-oligosaccharides are characterized by the structural formulae I and II which are shown on FIG. 1.

According to the invention, they are prepared by enzymatic hydrolysis starting from fucanes under the action of endofucanases, i.e. of enzymes which the applicant's company has had the merit to isolate.

These enzymes are secreted by a bacterium strain presenting a fucanolytic activity which was obtained by the applicant's company starting from industrial muds used for the treatment of the effluents rich in sulphated fucanes, of a plant for the extractions of alginates.

In that respect, the applicant's company worked as follows.

Muds, taken from the oxygenation and sedimentation or decantation basins of a sewage or purification plant located downstream of a plant for the extraction of alginates are used as an inoculum for a poor medium based on filtrated sea water containing 2 g/l of fucane.

Working on aliquot portions of the thus constituted culture medium there is carried out every day the test said "using seric bovine albumine" in acid medium (or BSA).

The principle of this test is based on the fact that anionic polysaccharides bind, in acid medium with positively loaded albumin thus causing the precipitation of the totality of the complexes which are formed.

On the contrary, olygosaccharides and oses are neither precipitated nor flocculated because their molecular weight is too low to cause the formation of an insoluble complex.

In view of the BSA test, 600 µl of the culture supernatant are introduced in a microtube having a capacity of 1 ml, the microtube being then subjected to centrifugation.

The supernatant, i.e. 500 µl, is transferred into another tube and mixed with 2 ml of the solution of acid BSA consisting of 3.26 g of sodium acetate, 4.56 ml of acetic acid ("glacial") and 1 g of BSA in 1 l of distilled water, the pH being from 3.72 to 3.78.

In parallel, a control is treated, this control being consisting of 500 µl of culture supernatant without inoculum.

Taking into consideration the preceding explanation, the formation of a cloudiness identical to that which occurs in the control shows that no degradation of the polymer occurred; on the contrary, in the case where the cloudiness is lower or even inexistent, it is possible to conclude that an enzymatic activity specific of fucane is present in the bacterial culture.

The test was noticed as being positive after 7 days of incubation of the fucane in the presence of the inoculum hereabove described.

An aliquot portion of the corresponding culture medium is then spread over a Petri box containing the medium known on the name Zobell-Fucane, which is consisting of the Zobell medium (1941) complemented with fucane to 2 g/l and solidified with agar to 15 g/l.

The composition of the Zobell medium [Zobell C E (1941) "Studies on marinebacteria. The cultural requirements of heterotrophic aerobes" published in J. Mar. Res., 4:41–75] is as follows:

| Bactopeptone Difco | 5,0 g |
| Difco yeast extract | 1,0 g |
| Filtrated Sea Water | 800 ml |
| Distilled Water | q.s.p. 1 l |

In the Petri box, the formation of a certain number of colonies is noticed, these colonies being different from each other and correspond to as many strains.

Each of these colonies, in other words each of these strains is isolated starting from that medium and introduced in a liquid Zobell-Fucane medium consisting of ½ volume of Zobell and ½ volume of a solution of fucane comprising 4 g/l in filtrated sea water.

On each of the thus isolated strains introduced in the Zobell-Fucane medium, the BSA test is carried out in order to detect the fucanolytic strains.

When the test is positive, the strain is seeded on the Zobell-Fucane medium to check whether it continues to hydrolyse the fucanes of the new medium; if yes, that means that all the genetic apparatus which is necessary to the production of fucanases is present; in that case it is considered that the strain is induced by the substrate; in other words, the presence of fucanes in the medium induces the production of the enzymes by the strain. For that reason, the BSA test is again carried out on the new culture.

Proceeding thus a strain has been isolated which was called SW5 and which gives raise to a positive BSA test after 3 to 4 days, when cultivated on the Zobell-Fucane medium.

The above said strain SW5, selected according to the way which has been described, was deposited under the number 12171 in the collection DSMZ (Deutsche Sammlung von Mikroorganismen und Zellkulturen GmbH) whose address is as follows:

Mascheroder Weg 1b, D-38124 Braunschweig, Germany.

The strain is a Gram-negative rod bacterium, strictly aerobic, chimiorganotrophic and heterotrophic. After 3 days culturing, the colonies on the solid Zobell-Fucane medium are small (1 mm diameter) and are pigmented in orange colour. The strain SW5 needs sea water for its growth, its optimal growth temperature being about 18–20° C. No growth at all is noticed at temperatures below 15° C. and above temperatures of 25° C. The other phenotypical characteristics of the strain SW5 are shown in the following Table I.

TABLE I

Physiological and biological features of the strain SW5

| Positive features | Negative features |
|---|---|
| catalase | oxydase |
| α-cyclodextrin | flexirubin |
| dextrin | reduction of nitrates |
| glycogen | formation of indol |
| cellobiose | fermentation arginin dihydrol |
| D-fructose | urease |
| L-fucose | tween 40 |
| D-galactose | tween 80 |
| gentobiose | N-acetyl-D-galactosamin |
| α-D-glucose | N-acetyl-D-glucosamin |
| α-D-lactose | adonitol |
| maltose | L-arabinose |
| D-mannose | D-arabitol |
| β-methyl-D-glucosid | erythritol |
| turanose | m-inositol |
| mono-metyle-succinate | lactulose |
| D-galacturonate | D-mannitol |
| D-glucuronate | D-melibiose |
| D.L-lactate | D-psicose |
| L-alanin | D-raffinose |
| L-alanyl-glycin | L-rhamnose |
| L-asparagin | D-sorbitol |
| aspartate | sucrose |
| L-glutamate | D-trehalose |
| glycyl-L-aspartate | xylitol |
| glycyl-L-glutamate | methyl pyruvate |
| L-ornithin | acetate |
| L-prolin | cis-aconitate |
| L-threonin | citrate |
| urocanate | formate |
| glucose-1-phosphate | D-galactanate lacton |
| glucose-6-phosphate | D-gluconate |
| | D-glucosaminate |
| | α-hydroxybutyrate |
| | β-hydroxybutyrate |
| | γ-hydroxybutyrate |
| | p-hydroxyphenylacetate |
| | itaconate |
| | α-ketobutyrate |
| | α-ketoglutarate |
| | α-ketovalerate |
| | malonate |
| | propionate |
| | quinate |
| | D-saccharate |
| | sebacate |
| | succinate |
| | bromosuccinate |
| | succinamate |
| | glucuronamate |
| | alininamide |
| | D-alanin |
| | L-histidin |
| | D.L-carnitin |
| | Y-aminobutyrate |
| | inosin |
| | uridin |
| | thymidin |
| | phenylethylamin |
| | putrescin |
| | 2-aminoethanol |
| | 2.3-butanediol |
| | glycerol |
| | D-.L-α-glycerol phosphate |

The philogenetic relations of strain SW5 have been established by way of the nucleotidique ID sequence No. 1 of the gene coding for ARN 16S.

The comparison of the sequence of this gene with the homologous genes from bacteria of the CFB group (Cytophaga-Flavobacterium-Bacterium-Bacteroïdes) has permitted to construct a phylogenetic tree from which it appears that the strain pertains to the family of *Flavobacteriaceae* (Bernardet et al, 1996, International Journal of Systematic Bacteriology, January: 128–148) and that it is close to *Gelidibacter algens* (Bowman et al, 1997, International Journal of Systematic Bacteriology, July: 670–677), a strain isolated from the Antarctic ices.

It follows that the process according to the invention for the preparation of the above said fuco-oligosaccharides is characterised by the fact that a substrate consisting of a raw material based on fucanes is subjected to an enzymatic hydrolysis using a fucanolytic enzyme or endofucanase obtainable from a bacterium strain deposited under the number 12171 in the DSMZ collection.

The bacterium SW5 is secreting in its culture medium significant amounts of fucanase activity which can be used at room temperature in a medium buffered at pH 7.5 or even in water.

The preparation of the substrate in other words of the fucanes which are intended to be subjected to the action of the enzymatic activity, is carried out as follows.

A quantity of 150 kg of brown algae *Pelvetia canaliculata* is subjected to a grinding in view of obtaining fragments from 2.5 to 3 mm, using a device denoted Comitrol 2100 and marketed by the company Urschel.

These fragments are subjected to an extraction using 800 l of hydrochloric acid 0.01 N containing 4% by weight of $CaCl_2$ with stirring during 3 hours at 70° C.

The suspension of fragments of algae thus treated is decanted during 2h30 and the thus obtained retentate is centrifuged; the supernatant obtained after the centrifugation is subjected to a tangential ultrafiltration on membranes of 50 kDa. The retentate obtained at the end of that tangential ultrafiltration is atomised using a device denoted Miro and marketed by the company Minor Production.

The result of said atomisation is a powder consisting essentially of fucanes.

That powder is subjected to a supplemental purification by redissolution, centrifugation, precipitation of the supernatant with ethanol, redissolution of the precipitate in water and tangential ultrafiltration of the aqueous solution on membranes of 30000 Da.

The residue obtained at the end of said ultrafiltration is subjected to a lyophilisation and constitutes the substrate looked for; it is denoted FS28EtOH.

That substrate, in other words that fucane powder, is subjected to the enzymatic activity obtained starting from the bacterium SW5.

In that respect, a solution containing 1 g/l of the substrate FS28EtOH in the buffer Tris (20 mM, pH 7,5) is prepared; an amount of 50 μl of that solution is taken and mixed with 10 μl of the proteinic fraction to be tested which contains the enzymatic activity obtained starting from bacterium SW5.

The mixture is maintained during 1 hour at room temperature.

The final hydrolysate contains the mixture of fuco-olygosaccharides in question.

That hydrolysate is subjected to an electrophoresis in view of showing in qualitative manner the presence of the oligosaccharidic fractions; that electrophoresis is carried out on polyacrylamide gel using the technique called C-PAGE disclosed by Zablackis E. and Perez J. (1990) in the article under the title "A partially pyruvated carrageenan from Hawaiian *Grateloupia filicina* (Cryptonemiales, Rhodophyta) published in "Bot. Mar." 33:273–276.

The degradation profiles of the fucanes obtained using the enzyme produced by the bacterium SW5 show that the enzymatic activity of the strain in question is of the endolytic type; it has been noted during the tests that the fucanes comprise structural elements which are similar to one another whatever the brown algae from which they are extracted.

The endo-fucanase activity of the strain SW5 has been purified to electrophoretic homogeneity; it has been determined that the protein in question has a molecular weight of about 105 kDa.

Three intern peptides have then been microsequenced.

The microsequences ID No. 2, ID No. 3 and ID No. 4 have thus been obtained.

The invention also relates to the endofucanases characterized by the fact that they contain sequences which are analogous to peptides ID No. 2, ID No. 3, ID No. 4 and/or ID No. 6 as well as the endofucanase genes characterised by the fact that they contain sequences which are analogous to the nucleotidique sequence ID No. 5.

The purification of the endo-fucanase activity hereabove referred to has been carried out using the device marketed under the designation FPLC$^R$ by the Company Pharmacia; this device has been put at 4° C.

After culturing during five days the strain SW5 in 6 l of Zobell-Fucane medium, a micro filtration was carried out on a device of the Pellicon type of the Company Millipore with a 0.45 μm (Millipore) cartridge and then a tangential ultrafiltration was carried out using a PTGC cartridge of 30 000 Da.

For the fractionation of the proteins, procedure is as follows:

With respect to the first fractionation from 0 to 40%, slowly and under slow stirring at 4° C., $(NH_4)_2SO_4$ having a concentration of 242 g/l is added to the proteinic solution. After dissolution of the totality of ammonium sulphate the solution is centrifuged; the residue which represents the fraction between 0 and 40% is not kept while the supernatant is subjected to a further fractionation from 40 to 60%. That fractionation is carried out by addition of $(NH_4)_2SO_4$ at a concentration of 130 g/l slowly and under gentil stirring at 4° C. As soon as the crystals are dissolved the solution is centrifuged; the residue, which represents the proteinic fraction between 40 and 60% of saturation of the ammonium sulphate, is kept and resolubilised in the buffer Tris 20 mM pH 7.5, NaCl 50 mM, $CaCl_2$ 5 mM, $MgCl_2$ 5 mM.

The fraction between 40 and 60% of saturation of the ammonium sulphate is diluted 20 times in the buffer Tris 20 mM pH 7.5 and resaturated at 40% of $(NH_4)_2SO_4$.

The thus obtained sample is introduced on a chromatographic column of hydrophobic interaction based on Phenyl Sepharose CL4B Pharmacia at the rate of 1 ml/min.

The column is previously balanced with the buffer Tris pH 7.5; $(NH_4)_2SO_4$ at 40%. The gradient takes place by decrease of the concentration in $(NH_4)_2SO_4$ from 1.8 M (40%) to 0 M in the buffer Tris in 3 volumes of column, and then using 2 volumes of buffer without $(NH_4)_2SO_4$.

Each proteinic fraction is used for the hydrolysis of the fucane FS28EtOH. The hydrolysate is prepared as indicated hereabove by addition of the said fraction to a solution of fucane at a concentration of 1 g/l in the buffer Tris 20 mM pH 7.5 containing salts. The hydrolysate is then tested using the technique C-PAGE. The fractions called "positive on C-PAGE" are those which generate an electrophoretical profile containing fractions of oligofucosaccharides.

The fractions which provide a positive degradation profile on polyacrylamide gel are collected and diluted 5 times in buffer Tris 20 mM pH 7.5; NaCl 5 mM before being injected on a chromatographic column for anion exchange loaded with DEAE Sepharose CL6B marketed by the Company Pharmacia.

The proteins are eluted by a NaCl gradient from 5 mM to 1 M in 3 volumes of the column, at 1 ml/min.

These fractions are then introduced in quantities of 100 μl on a filtration column, loaded with Superdex 200 gel marketed by the Company Pharmacia and previously balanced at 0.5 ml/min in sodium phosphate buffer 50 mM pH 7.0; NaCl 150 mM.

The active fraction identified by the C-PAGE technique is collected and the purity of the protein is determined on a SDS gel at 12.5% using the device Phast-System$^R$ of the Company Pharmacia. The molecular markers used are standards from 14.5 to 200 kDa marketed under the name "broad-range" by the Company Biorad.

Starting from the proteinic microsequences SEQ ID No. 3 and SEQ ID No. 4, oligonucleotides were synthesized; these oligonucleotides were used as starters in view of synthesizing by PCR (Polymerase Chain Reaction) a fragment of the gene coding for fucanase, the purified DNA of the SW5 strain playing the role of a matrix for the reaction.

The specific PCR products of these starter pairs have been sequenced.

One of them presents the nucleotidic sequence SEQ ID No. 5.

The derived proteinic sequence whose length is 67 amino acids contains the microsequences SEQ ID No. 3 and SEQ ID No. 4, which means that it is a fragment of the fucanase of the strain SW5.

The nucleotidic sequence SEQ ID No. 5 is consequently a portion of the gene having a length of 203 nucleotides, which encodes the fucanase of the strain SW5.

For the preparation of the fuco-oligosaccharides, it is possible to use several methods, two of which are hereafter described.

According to a first method, the enzyme acts until complete consumption of the substrate, during 24 hours; a fucoïdane of *Pelvetia canliculate* is incubated in the presence of the partially purified enzyme and then the hydrolysis products are ultrafiltrated on a membrane of 500 Da. A fraction denoted I27 is thus obtained.

From the practical stand point of view, a fucane extracted from *Pelvetia canaliculata* (fraction FS28EtOH) is hydrolysed at room temperature during 24 hours, by addition of an amount of 30 ml of a precipitate of enzyme with ammonium sulphate 40–60% (3.02 mg of proteins) to 1 liter of substrate having a concentration of 5 g/l in the buffer Tris 20 mM pH 7.5; NaCl 50 mM; $MgCl_2$ 5 mM.

The thus obtained hydrolysat is complemented with distilled water until 20 l, and then subjected to an ultrafiltration on a tangential ultrafiltration system of 10 000 Da using a 0.46 m$^2$ PTGC cartridge of the Company Millipore with an entrance pressure of 6.5 bar and an exit pressure of 5.5 bars.

The thus obtained ultrafiltrate is recovered and ultrafiltrated again on 500 Da using the device marketed under the trademark Omega Centraset OM500DC05 by the Company Pall Filtron with 1 bar at the entrance of circuit and with a pressure equal to zero at the exit; that further tangential ultrafiltration is intended to remove the salts of the ultrafiltrate.

In view of the fractionation of the oligomers the residue is again ultrafiltrated on 500 Da the pressure being however equal to 2.5 bars at the entrance and 2 bars at the exit.

The filtrate which passes the threshold of 500 Da (about 20 l) of the membrane is then concentrated on a rotary evaporator, neutralised with ammonium carbonate and then lyophilised using the device marketed under the trademark Lyolab A LSL by the Company Secfroid. The lyophilisate which is thus obtained contains the oligofucanes called I27.

The oligofucanes of the fraction I27 thus obtained have been subjected to a supplemental fractionation by ions exchange chromatography and exclusion chromatography.

Figure 2:
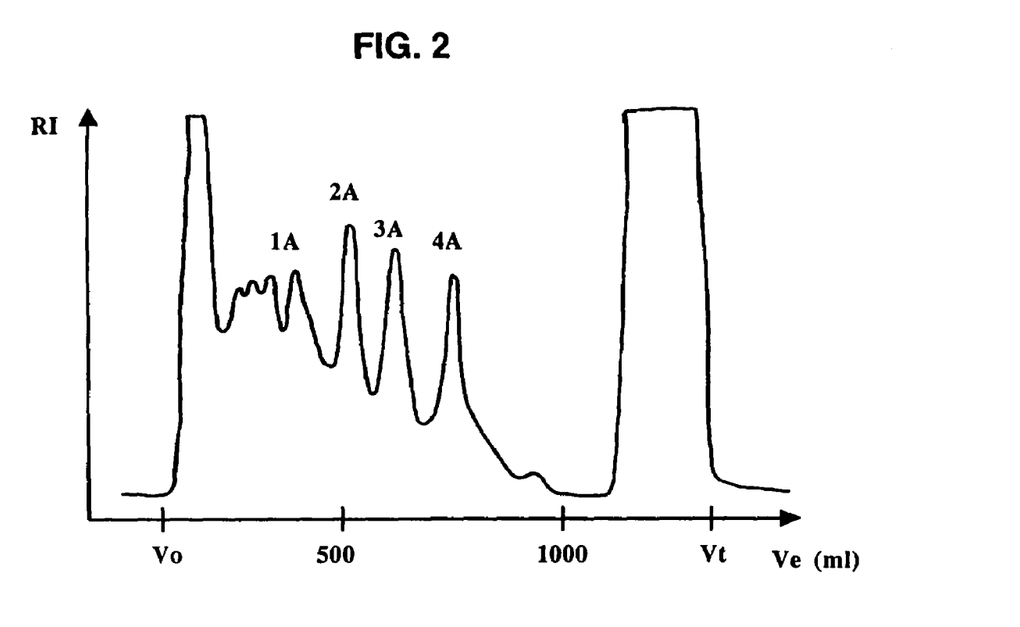

The exclusion chromatogramme obtained on a gel of the trademark BIOGEL P6 is reproduced on the drawing of FIG. 2 which shows on the x-axis the elution volume (Ve) expressed in ml and on the y-axis the refractometric indice (RI) aussi eluat.

The structure of the thus obtained oligosaccharides (pics 1A to 4A of chromatogramme) has been analysed by bidimensional RMN.

The pics 4A and 3A respectively correspond to a tetrasaccharide and a hexasaccharide formed by the residues of fucose alternatively linked by α (1->3) and α (1–4) links and sulphated on carbone atom 2 (FIG. 1).

The pics 2A and 1A are, as far as they are concerned, constituted by mixtures of variable DP of oligosaccharides of the same homologous series but can be branched.

That result suggests that the starting polysaccharides are constituted at least partially by the repetition of α-L-Fuc-2-sulfate-1->3-α-L-Fuc-2-sulfate-1->4 not disclosed to date.

A second method comprises a continuous hydrolysis; it consists, using an ultrafiltration membrane of 30 kDa, to withdraw from the action of the enzyme the oligofucanes when they are formed. The thus obtained fraction is denoted "fraction I25" and contains oligofucanes of molecular weight higher than that of those constituting the fraction I27.

From the practical point of view, the substrate (50 g of FS28EtOH) is dissolved in 10 liters of distilled water.

In order to carry out the hydrolysis, 25 ml of enzyme in the form of a fraction precipitated by ammonium sulphate between 40 and 60% of saturation in 2 liters of substrate; the continuous ultrafiltration is started after 30 minutes.

For that tangential ultrafiltration, a device of the trademark Pellicon which comprises a 30 000 Da cartridge is used the said device being adjusted on 1 bar at the entrance and 0 bar at the exit during the full duration of the hydrolysis.

The exit of the filtrate is partially closed in order to maintain the filtration output at 2 l/h.

The characteristic features of the reaction vessel are selected in order to permit supplying the enzyme with substrate until exhaustion of the 10 liters and maintenance of a fixed hydrolysis volume of 2 liters.

The hydrolysis is continued by addition of distilled water (8 liters) continuously until the moment at which the filtrate no longer contains oligomers.

A quantity of 18 liters of an ultrafiltrate is thus obtained and concentrated to about 1 liter using a device Pellicon equipped with a cartridge of 500 Da, the entrance pressure being 2 bars and the exit pressure 0; a supplemental concentration until 200 ml is carried out by rotary evaporation, the concentrate being then neutralised and lyophilised.

The filtrate which contains the low molecular weight fractions (i.e. suitable to go through a membrane at the threshold of 500 Da) has not been kept.

The fraction I25 denotes the oligofucanes retained between the thresholds of 500 Da and of 30000 Da.

The biological activity of the fractions I27 and I25 on plants has been examined.

The direct elicitor effect of these fractions has been analysed on cultures of cells of tobacco BY.

Five markers of the defence reaction have been tested independently, namely:
the alcalinisation of the culture medium (early response currently observed when the plants are incubated in the presence of oligosaccharidic elicitors),
the activity levels "phénylammonia lyase" (PAL) which is a key enzyme for the synthesis of phytoalexins in the plants,
the activity levels O-methyl transferase (OMT) which is an enzyme envoloved in the synthesis of lignin,
the activity levels lipoxygenase (LOX) which is an enzyme envoloved in the generation of methyle jasmonate, one of the elements of the cascades of signalization which results in the activation of the defence genes and
the contents of salicylic acid (SA) which is an other secondary messenger envoloved in the defence reactions.

The fraction I27 administered at a dosis of 200 mg/l, induces an alcalinisation of the culture medium of the tobacco cells from 1 to 1.5 pH units. With respect to the non treated cells, the activities PAL and OMT are respectively stimulated by a factor 50 to 600 and 2.0 to 2.8 between 4 hours and 8 hours after the addition of I27 to the culture medium.

The LOX activity, measured 18 hours after the addition of I27 at the dosis of 200 mg/l is 7 times more important than that of the control cells. Similarly, 3 hours after the beginning of the treatment, the contents in salicylic acid are 70 times more important than in the non treated cells.

Analogous results have been observed using the fraction I25. A stronger stimulation of the LOX activity has however been noticed, until a multiplicative factor of 55 with respect to the control cells.

Figure 3:
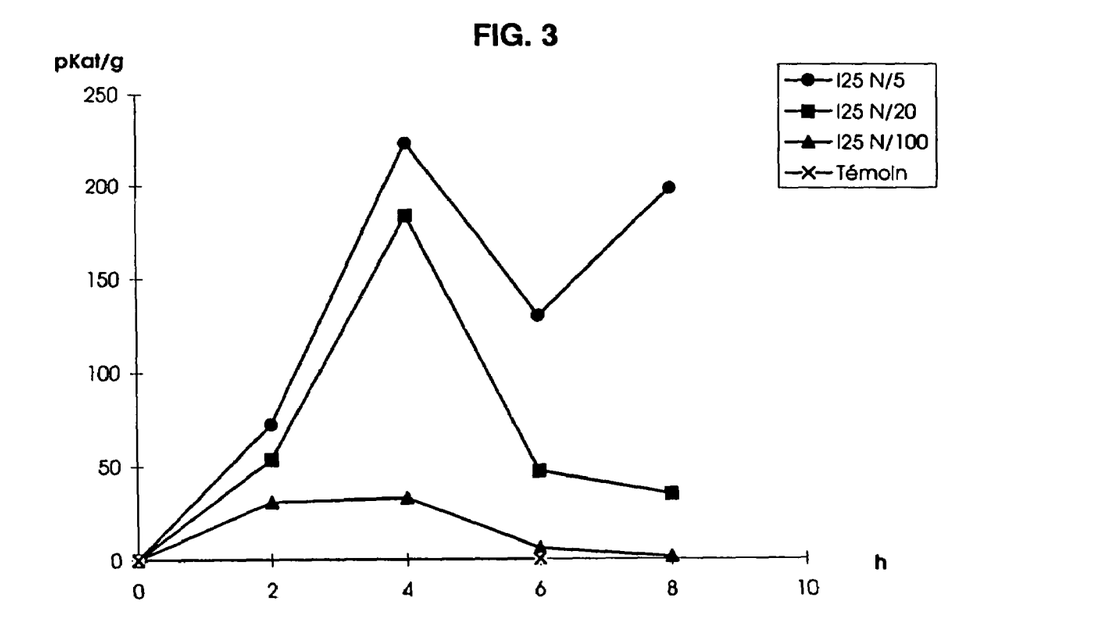

FIG. 3 shows the influence of the fraction I25 on the stimulation of the PAL activity in the tobacco BY cells; it shows the variation of the activity expressed in pico-katal per g (pKat/g) of fresh mass of cellular suspension in function of the time expressed in hours for three concentrations, i.e. 200 mg/l, 50 mg/l and 10 mg/l and for a control.

Examination of FIG. 3 shows that concentrations of 10 mg/l are sufficient to identify a significant stimulation with respect to the controls cells which are non elicited and a saturation of the response is observed for concentrations higher than 50 mg/l.

The result of these experiences show that the oligofucanes according to the invention are recognized as elicitors by the tobacco cells.

With respect to non treated cells, they stimulate in a very strong manner (i.e. in proportions which are comparable to those of other elicitors such as the oligopectines and the oligo α1–3 glucanes), the PAL, LOX and OMT activities as well as the contents in SA.

The elicitor effect of the fraction I25 has also been analysed on wheat cellular suspensions.

It has been shown that this fraction induces the PAL activity.

In that respect, at the concentration of 200 mg/l, I25 has stimulated by a factor of 15 to 20 the PAL activity between 2 and 6 hours after the treatment.

A dosis of 50 mg/l still stimulates the PAL activity by a factor of 4, 4 hours after the treatment.

I25 also induces the PAL activity in parsley cellular suspensions.

At the concentration of 200 mg/l I25 has stimulated by a factor from 15 to 30 the PAL activity between 4 and 6 hours after the treatment.

A dosis of 20 mg/l still stimulates the PAL activity by a factor of 5, 4 hours after the treatment.

By way of another series of experiences, it has been shown that infiltrated in tobacco leaves, the fuco-oligosaccharides protect against the VMT (virus of the tobacco mosaic). The experiences have been carried out as follows.

The fraction of fuco-oligosaccharides denoted I25 (200 mg/l) is infiltrated using a syringe in three tobacco leaves (leaves 4, 5 and 6 starting from the bottom) which were two months old.

Five days after the infiltration, an inoculation with VMT is carried out in the leaves 5, 6 and 7, the leave 4 being the control.

One week after the inoculation, the number of injuries (NL) and the size of these injuries (TL) on the leaves of the plants treated as well as of the plants only treated with water were determined.

In Table II hereafter are indicated the percentages of protection according to the two criteria hereabove defined.

TABLE II

Protection of tobacco against the VMT by the fuco-oligiosaccharides

| | % protection (NL) | % protection (TL) |
|---|---|---|
| Leave 5 | 65 | 25 |
| Leave 6 | 65 | 35 |
| Leave 7 | 40 | 26 |

Leave 4 does not show any injury.

From the results collected in the table, it is possible to conclude that a protection was induced in the leaves infiltrated with I25 (leaves 5 and 6), but also in leave 7 which had not received fuco-oligosaccharides.

It is thus possible to talk about a systemic protection.

From these two series of experiences on wheat, parsley and tobacco, it appears that the fuco-oligosaccharides stimulate enzymatic activities which are natural defence markers not only in the case of tobacco, but also in the case of wheat and parsley.

That stimulation results in a systemic protection against the VMT and probably against other phytopathogenic agents.

By way of illustration, two examples are hereafter described.

EXEMPLE 1

Liquid concentrate for agriculture based on oligofucanes:

| | |
|---|---|
| Olygofucane I25 | 0,200 kg |
| Tween 801 | 0,005 kg |
| Solic methylparaben | 0,005 kg |
| Water | 0,790 kg |
| Total | 1,000 kg |

That concentrate is used after dilution in 1000 liters of water of a quantity comprised between 10 g and 10 kg, preferably between 20 g and 5 kg and still more preferably between 100 g and 1 kg; that dilution corresponds to a content in oligofucanes I25 comprised between 2 and 2000 g, preferably between 20 and 200 g for 1000 liter de water.

EXEMPLE 2

Soluble concentrated powder comprising as active substance the hydrolysate I27 as well as adjuvants.

For 1 kg weight/weight, the constitution of that powder is defined as follows:

| | |
|---|---|
| Oligofucane I27 | 0,200 kg |
| Kaolin | 0,495 kg |
| Mannose | 0,050 kg |
| Sodic methylparaben | 0,005 kg |
| Purified starch | 0,250 kg |
| Total | 1,000 kg |

That powder is used after dilution in an amount of water sufficient to obtain a composition whose contents in oligofucane I27 is comprised between 2 and 5000 g, preferably between 20 g and 100 g for 1000 liters of water.

What is claimed is:

1. A method of treatment for stimulating a direct elicitor effect of defense reactions in a plant comprising:

selecting a sulphated fuco-oligosaccharide having a polymerization degree from 4 to 100 α-L fucose units;

forming an aqueous solution having a concentration of the sulphated fuco-saccharide of at least 10 mg/l; and applying the said solution to the plant to be treated.

2. The method of treatment according to claim 1, wherein the sulphated fuco-oligosaccharide has the following structure I:

3. The method of treatment according to claim 1, wherein the sulphated fuco-oligosaccharide has the following structure II:

4. The method of treatment according to claim 1, wherein the plant is tobacco.

5. The method of treatment according to claim 1, wherein the plant is wheat.

6. The method of treatment according to claim 1, wherein the plant is parsley.

* * * * *